United States Patent [19]

Karnis et al.

[11] 4,342,618
[45] Aug. 3, 1982

[54] METHOD AND APPARATUS ON-LINE MONITORING OF FIBRE LENGTH OF MECHANICAL PUMPS

[76] Inventors: Alkibiadis Karnis, 487 Montcalm Ave., Dollard des Armeaux, Quebec, Canada; Paul M. Shallhorn, 159 Bastien, Vaudreuil, Quebec, Canada, J7V 5X9

[21] Appl. No.: 196,767

[22] Filed: Oct. 14, 1980

Related U.S. Application Data

[63] Continuation-in-part of Ser. No. 38,587, May 14, 1979, abandoned.

[51] Int. Cl.³ .................... D21F 7/06; G01N 21/00
[52] U.S. Cl. .................... 162/49; 73/61 R; 162/55; 162/198; 162/263; 209/208
[58] Field of Search .............. 73/61 R, 61.4; 209/207, 209/211; 162/49, 198, 263, 55, DIG. 10

[56] References Cited

U.S. PATENT DOCUMENTS 3,802,964  4/1974  Forgacs et al. ............... 162/263

OTHER PUBLICATIONS

Karnis et al., "Mechanical Pulp Mill Control Systems, I. The Measurement of Fibre Length" presented at Canadian Pulp & Paper Assoc. Jun. 1971.
Tusman, "The Fiber Length of Bauer-McNett Screen Factors", TAPPI, vol. 55, No. 1, Jan. 1972.
"Fiber Length of Pulp by Classification", TAPPI Standard T2330575, 1975.

*Primary Examiner*—Steve Alvo

[57] ABSTRACT

A method and an apparatus for determining the fibre length distribution by weight of a pulp and a method and apparatus for determining absolute consistency are disclosed.

The fibre length distribution is obtained by dividing the flow of a pulp sample into two separate flows, fractionating each of the flows by a screen into a retained and a through fraction, the screens being of different mesh sizes, measuring the amounts of each of a selected one of said retained or through fractions and determining, based on the cumulative normal distribution relationship of cumulative retained fraction in % of feed to fibre length, the fibre length distribution of the pulp sample.

7 Claims, 7 Drawing Figures

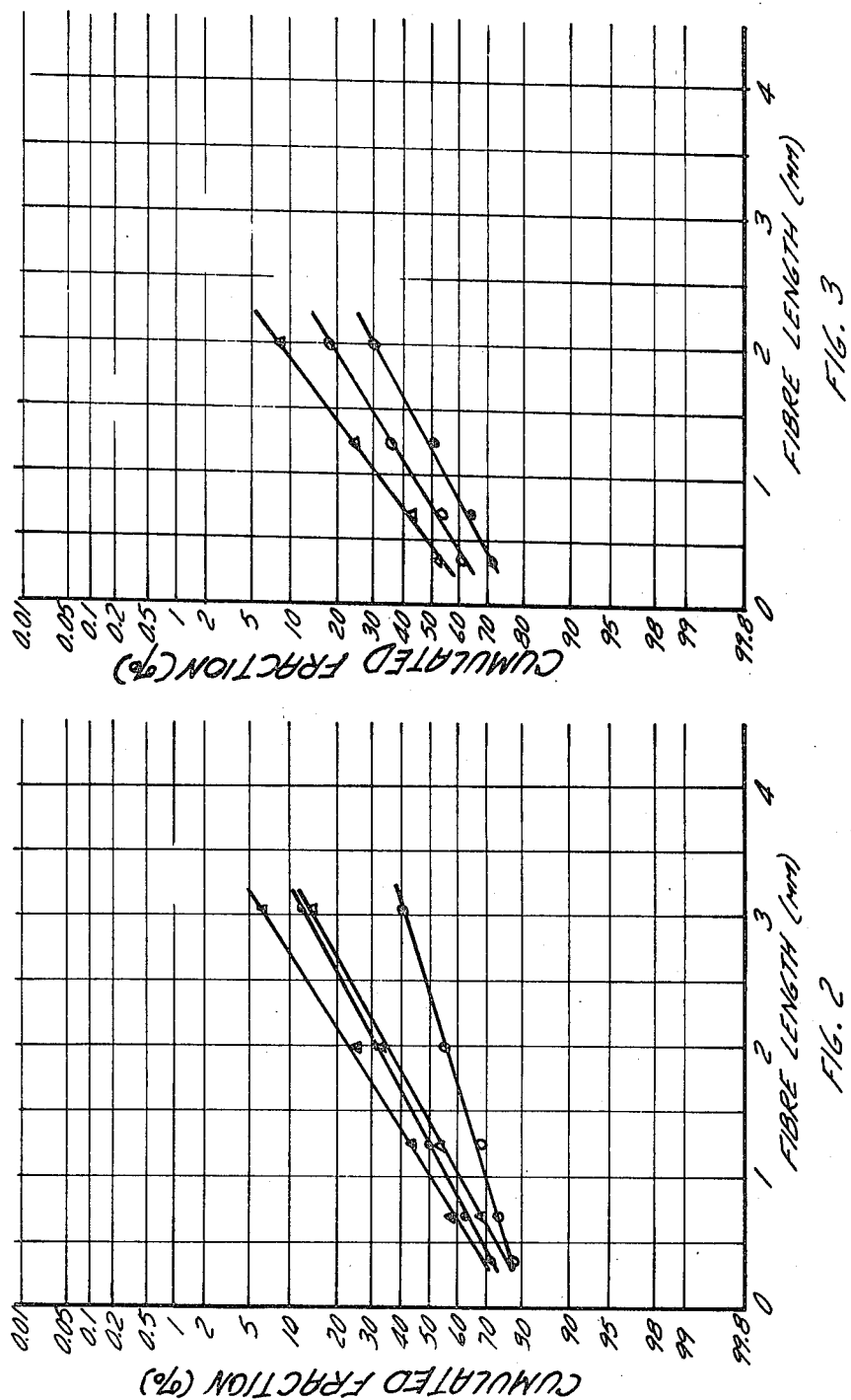

METHOD AND APPARATUS ON-LINE MONITORING OF FIBRE LENGTH OF MECHANICAL PUMPS

This application is a continuation-in-part of application Ser. No. 038,587, filed May 14, 1979 (now abandoned).

FIELD OF INVENTION

The present invention relates to a method and apparatus for on-line monitoring of physical properties of a mechanical pulp. More specifically, the present invention relates to a method and apparatus for determining, on-line, the fibre length distribution by weight and/or the average fibre length of a mechanical pulp and a method and apparatus for on-line determination of consistency of a pulp suspension substantially free of other characteristics of the fibre.

BACKGROUND OF THE INVENTION

By the term mechanical pulps is understood pulps produced primarily by mechanical processing with or without auxiliary steps of chemical or physical nature, such pulps include conventional (stone) ground wood and refiner groundwood and pulps produced by an array of chemi-mechanical and thermo-mechanical processes.

It has been stated for example in U.S. Pat. No. 3,802,964 issued Apr. 9, 1974 to Forgacs and Karnis that the fibre characteristics of average specific surface and particularly of average fibre length are important in determining the properties of a paper produced from said pulp. The average fibre length is very important for predicting tensile, bursting, tearing and wet web strengths and also affects light scattering coefficient (opacity) while the fibre length distribution is important in relation to tear strength since for a given average fibre length generally the wider the distribution the higher the tear strength. However, no on-line methods of determining average (median) fibre length or fibre length distribution are available and such determinations could only be made in a laboratory.

It has been proposed to determine the L-factor (which is defined as the total amount of pulp retained on the 48-mesh screen of a Bauer McNett fibre length Classifier expressed as a percentage by weight of the feed) or weight-average fibre length by the weight ratio of a through or retained fraction to the feed as described in U.S. Pat. No. 3,873,416 issued Mar. 25, 1975 to Forgacs and Karnis, but, as above indicated, notechniques are available for determining, on-line, the fibre length distribution by weight of a mechanical pulp.

Consistency meters currently used in the pulp and paper industry measure consistency indirectly i.e. they measure other properties of the pulp, such as resistance to flow, dielectric properties of the pulp suspension etc. which properties are related to consistency as well as other fibre properties.

It has been proposed to measure consistency substantially independent of other pulp properties using the Sperry Gravity Master (see Management & Control, Vol. 1, Nov. 11, 1968, pp T179–T186) which claims an accuracy for consistency over the range of 0.4 to 1.5% within the range of 12 to 3% of the consistency measured. This instrument operates on the technique of continuously measuring the weight of stock flowing through a specific volume of pipe.

It has also been proposed by Thiessen and Dagg, published in the Pulp & Paper magazine of Canada September 1959 to measure consistency by recording the vibrations resulting from rotation of an unbalanced rotor, the degree of unbalance being determined by the difference in weight between given amount of water with the same amount of pulp slurry.

Neither of the above devices have proved to be commercially satisfactory. No instrument for on-line measurement of pulp consistency substantially free of other characteristics of the pulp is currently known.

BRIEF DESCRIPTION OF THE PRESENT INVENTION

The object of the present invention is to provide a method and apparatus for on-line determining the average fibre length and/or fibre length distribution by weight of a mechanical pulp.

Another object of the present invention is to provide a method and apparatus for on-line determination of the absolute value of consistency.

Broadly the present invention relates to a method and apparatus to determine the fibre length distribution by weight of a mechanical pulp which comprises, feeding said pulp into two flows, measuring the required parameters of said flows to determine their fibre mass flow rates and determining the fibre mass flow rates, fractionating each of said flows by screening means into a retained and a through screen fraction, the screening means factionating one of said two flows having a different mesh size than the screening means fractionating the other of said two flows, means for measuring required parameters of a selected one of said retained fractions or said through fractions for each of said flows to determine their fibre mass flow rates and determining their fibre mass flow rates, determining, based on said fibre mass flow rates and a cumulative normal probability distribution relationship of cumulative weight fraction as a percent of feed of fibre length.

The present invention also broadly relates to a method of measuring consistency of a pulp suspension which comprises continuously passing the pulp suspension through a density cell composed of a tube, preferably a substantially U-shaped tube, continuously mechanically vibrating said tube as said slurry passes therethrough, continuously measuring the frequency of vibration of said tube and converting said frequency to an indication of absolute consistency.

BRIEF DESCRIPTION OF THE DRAWINGS

Further features, objects and advantages will be evident from the following detailed description of the preferred embodiments of the present invention taken in conjunction with the accompanying drawings and which:

FIGS. 2 and 3 are plots of cumulative retained fraction in percent of feed vs fibre length in millimeters, on cumulative normal probability paper for several different pulps.

DETAILED DESCRIPTION OF THE PREFERRED EMBODIMENTS

Figure 1:
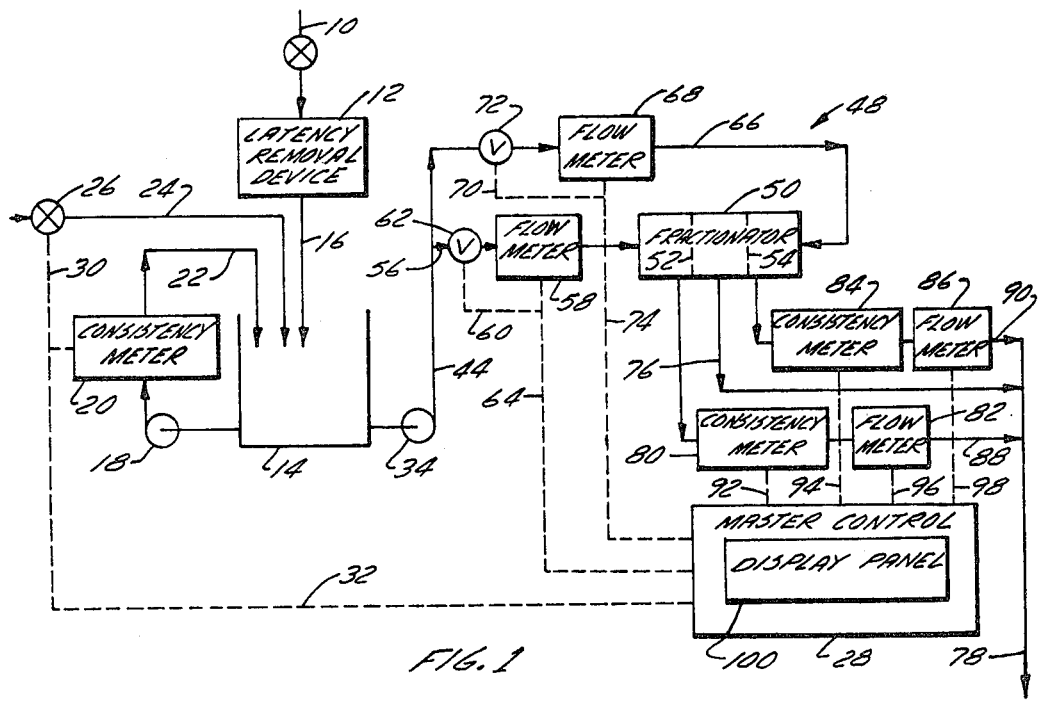
FIG. 1 is a schematic illustration of the process control of the present invention.

As shown in FIG. 1 a sample of mechanical pulp bled off from the process enters the system by line 10 and depending on the point in the pulping arrangement from which the sample is taken, it passes through a latency removal device 12 and then enters the container 14 via the line 16.

A suitable principle for liberating the latent properties in mechanical pulp relatively quickly is used in a laboratory device sold by Noram Quality Control and Research Equipment Ltd. This device releases the latent properties of a mechanical pulp by rapidly recirculating through a centrifugal pump (the pulp being at a temperature of about 90°–95° C.).

Pulp from the container 14 is pumped via pump 18 to consistency meter 20 and returned to the container 14 via line 22.

Requirements of a consistency meter 20 for use in an on-line monitoring system are such that it should measure consistency independent of other fibre properties (i.e. fibre lengths and specific surface) and should be capable of measuring absolute consistencies with an accuracy and reproducability within ±5% of the consistency measured. Thus in consistency meters for use in the present invention the principle for consistency determination should be a direct one, namely it should be based on the definition of consistency.

It is essential when measuring consistency using density meters, that the sample be substantially free of or contain no air or significant quantities of extraneous matter, or alternatively that there be no air in the sample and that the quantity of any extraneous material with the fibres (fillers, etc) be accurately known before the consistency can be determined. Also it is important that the temperature be set, since a change in temperature changes the accuracy of the instrument although the instrument may be calibrated for different temperatures.

Figure 4:
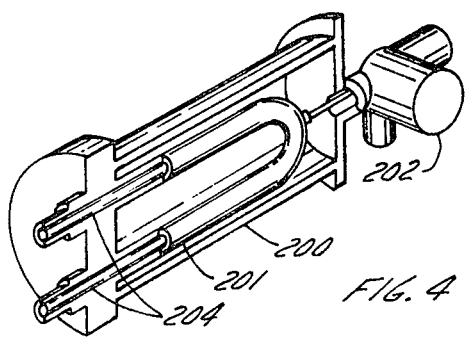
FIG. 4 is a schematic cross action of a density cell.
Figure 5:
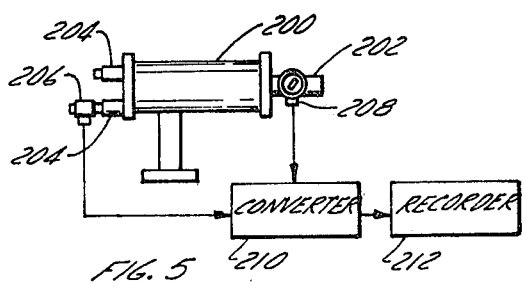
FIG. 5 is a schematic illustration of the density cell arranged to indicate consistency.

Such a consistency meter as illustrated in FIG. 4 comprises a density cell 200 having a U-tube 201 through which the pulp sample passes. This U-tube is vibrated by a suitable mechanism schematically illustrated at 202 about the node points indicated at 204. Suitable temperature and frequency pick-up devices are provided as indicated in FIG. 5 at 206 and 208 respectively and the output from these pick-up devices is fed to a convertor 210 which in turn feeds a strip recorder 212 or like instrument that indicates consistency of the pulp.

The density cell 200 used to obtain the results reported herein is a "Dynatrol" cell sold under the trade namer Cl-10H manufactured by Automation Products, Houston, Tex. This equipment is used to measure the density of samples however, when applied to pulp in a consistency range of about 0.1 to 1.5% has been found to provide an indication of absolute consistency of the pulp within the accuracy required for obtaining the fibre length distribution.

The "Dynatrol" cell referred to hereinabove was used to measure consistency and produced the results indicated in FIG. 6 i.e. the meter output corresponded very reproducibly with consistency based on five repeat runs at the same stone groundwood pulp. Similarly the accuracy for different types of chemical, groundwood and thermomechanical pulps is illustrated in FIG. 7.

It will be apparent that the consistency meter of the present invention provides a relatively accurate indication of the absolute consistency.

In the operation of the device, it is important that the stock be diluted with water substantially free of impurities to the consistency for measuring otherwise impurities in the dilution water may effect the ultimate reading of the consistency meter. Thus, for example, in the operation of the present invention on thermo-mechanical pulp the pulp will be diluted from the relatively high consistency leaving the refiner down to the consistency within the operating range of the density cell by the addition of water substantially free of impurities rather than white water or the like. It will be apparent that, by using significant amounts of dilution water substantially free of impurities, the consistency measurement will be quite accurate.

The operation of the consistency meter is relatively simple in that the stock diluted to the required consistency for operation in the density cell i.e. within the range 0.1 to 1.5% consistency is continuously fed through the U-tube 201, the U-tube is vibrated via the driver 202 and the frequency of the vibrations is determined via the sensor 208. This information is fed to the convertor 210 which in turn operates the recorder 212 or other suitable indicating instrument. While the instrument used has a U tube, the shape of the tube could probably be changed with appropriate other changes in the equipment.

Figure 6:
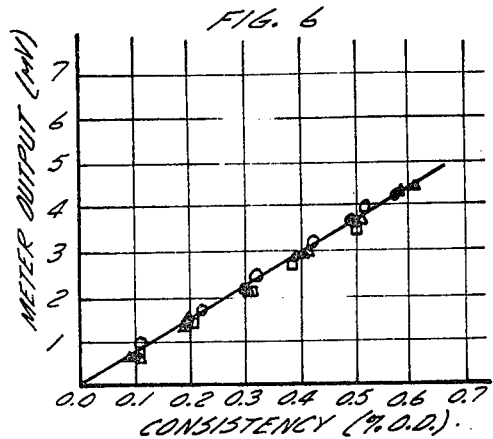
FIG. 6 illustrates the reproducibility of the correlation of consistency percent oven dried to the meter output in milli volts for a stone groundwood pulp.
Figure 7:
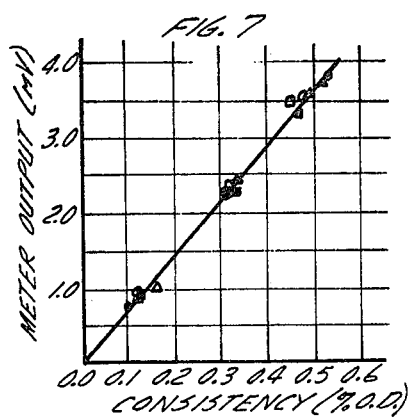
FIG. 7 is a graph of consistency vs meter output in milli volts for a plurality of different pulps.

$R^2$, the Coefficient of Determination for the plots of consistency vs meter output in FIGS. 6 and 7 is equal to about 0.99, clearly indicating very accurate correlation of consistency to meter reading.

Obviously to determine the density of a pulp slurry above of said range of 1.5%, at least a portion of the slurry must be diluted to within said range using fresh water, the amount of fresh water added noted and used to calculate the consistency of the pulp based on the measured consistency of the diluted portion.

In any event, the consistency meter 20 measures a consistency of the stock in the container 14 and preferably adjusts the water input through line 24 via control valve 26 to maintain the consistency of the stock in the container 14 substantially constant. The consistency meter 20 is connected to the valve 26 via control line 30 and to the master control 28 via line 32. In the event that the consistency in the tank 14 is always maintained constant, the control line 32 may be omitted since it will not be variable in the system.

Stock in the tank 14 is circulated via a pump 34 and line 44 to the fibre length monitoring instrumentalities 48 which include a fractionator 50 having two screens of different size openings (mesh sizes) as indicated at 52 and 54.

The screen 52 is fed from line 44 via line 56 at preferably a constant feed rate controlled by the flow meter 58 which as indicated via line 60 regulates the valve 62. The output of this flow meter 58 may be also directed to the master control 28 via the line 64. However, if the flow in the line 56 is held constant, obviously the input to the master control 28 via line 64 may be omitted.

Similarly stock flows to the screen 54 via line 66 preferably at a constant feed rate controlled by the flow meter 68 connected via control line 70 to the valve 72. The flow meter 68 is also connected via line 74 with the master controller 28 but this control line 74 may be omitted if the flow in line 66 is at a fixed rate.

In the illustrated arrangement, the through fractions of the two screens 62 and 64 are combined and fed via line 76 to line 78 which returns the pulp to the system. The retained fractions of screens 52 and 54 respectively are measured by a consistency meter 80 and flow meter 82 and consistency meter 84 and flow meter 86 respectively and are then fed via the lines 88 and 90 respectively to the line 78. The consistency meters 80 and 84 are connected to the master controller via lines 92, 94 respectively while the flow meters 82 and 86 are connected to the master control 28 via lines 96 and 98 respectively.

In the illustrated arrangements the two retained fractions are measured, if desired, the two through fractions may be maintained separate and these fractions measured instead or a combination of through and retained fractions measured (i.e. the through fraction of one screen and the retained fraction of another).

Screen sizes for the screen 52 and 54 may, for example, be 41 mesh and 35 mesh. Other combinations and screen size may also be used, however, care must be taken in selecting the size of the screen as if too large a mesh size is used fibres may tend to wrap around the screen and produce unacceptable results and if too fine a screen size is used the sensitivity of the instrument is reduced significantly. Generally the screens should be selected to between about 30 mesh and 50 mesh and preferably between 35 and 45 mesh.

The amount of pulp retained on the 41 mesh screen may be related to the R-48 fraction of the Bauer-McNett Classifier, which determines the L-factor for the pulp which has been found to be a useful measurement in determining the characteristics of a given pulp. The pulp retained on the 35 mesh screen can be related to the R-28 fraction of the Bauer-McNett Classifier.

Relationships have been obtained by developing regression equations based on experimental results for the 41 mesh screen $$(WF)_{41} = L + B(R-48)C + AC + D(R-48) \qquad 1$$

and similarly for the 35 mesh screen $$(WF)_{35} = L_1 + B_1(R-28)C_1 + A_1C_1 + D_1(R-28) \qquad 2$$

where L, B, A, D and $L_1$, $B_1$, $A_1$, $D_1$ are constants and C, $C_1$ are the consistencies of the stock and WF is the weight fraction for the specific screen indicated.

As a given consistency, equations 1 and 2 can be written $$(R-48) = K(WF)_{41} + P \qquad 3$$

and $$(R=28) = K^1(WF)_{35} + P^1 \qquad 4$$

where again K, $K^1$, P, $P^1$ denote constants determined experimentally. The weight fractions of 41 and 35 mesh screen are measured by obtaining the consistency and flow rate of each such retained fraction relative to the flow and consistency of the feed pulp to the screens.

Furthermore it has been found that a cumulative normal probability distribution relationship exists between cumulative retained fraction as percent of feed and fibre length (as defined by Tasman Tappi Vol. 55 No. 1 January 1972, i.e. the average fibre length obtained from the fibre length classification results from the Bauer-McNett Classifier). Four different pulps were fractionated on the conventional lab Bauer-McNett fractionator and the results were plotted on cumulative normal probability paper showing cumulative retained fraction in percent of feed vs fibre length in FIG. 2. The closed triangles are points determined for a first groundwood pulp, the open triangle for a second groundwood pulp, the closed circle for a first thermo-mechanical pulp and the open circles for a second thermo-mechanical pulp.

The plots are very accurate straight lines and thus determining any two points on any one of the curves will define accurately the fibrelength distribution of the pulp over a significant range including the median fibre length which is a fibre length whereby 50% of the fibres are longer and 50% are shorter.

While only four pulps have been plotted, in FIG. 2 numerous plups have been tested and all have resulted in similar straight lines. However, if a pulp contains an excess of fine material ($-200$ mesh) the straight line relation may not hold at the lower end of the lines.

To test other results the pulp fractions defined in "Characterization of Mechanical Pulps", Pulp & Paper magazine of Canada, convention issued PT-829, 1963 by Forgacs have been plotted in a similar manner on normal probability paper and also quite clearly generated in straight lines (see FIG. 3).

The distribution of fibre length can thus be obtained based on these findings.

The weight fractions (WF) in equations 1 and 2 can be calculated if the incoming fibre flows to the fractionators are known or kept constant via the flow meters 58 and 68 and the consistency and flow of the retained fractions as measured by instruments 80 and 82 for the screen 52 or 84 and 86 for the screen 54 via the equation.

$$WF = (C_r F_r / C_f F_f) \qquad 5$$

where WF equals the weight fraction $C_f$ and $F_f$ equal the consistency and flow of fibres flowing to the screen 52 or 54 respectively and $C_r$ and $F_r$ are the consistency and the flow of the retained fraction of screen 52 or 54.

The above relations are used to obtain the weight fraction from the on-line screens by equation 5, for say, the retained 35 and retained 41 mesh screens and then to convert these values to the Bauer-McNett classification by equations 1 and 2 or 3 and 4 respectfully. These converted values may then be plotted as fibre length (based on the average fibre lengths in Tasman reference referred to above) on normal probabilty paper. In this manner the input of the various meters to the master control 28 may be used to determine the fibre length characteristics of the pulp including the fibre length distribution, mean fibre length, L-factor etc. which may be displayed on suitable charts or gauges on the display panel 100.

Modification may be made without departing from the spirit of the invention as defined in the appended claims.

We claim:

1. A method for on line determining the fibre length distribution by weight of a pulp comprising, feeding said pulp in two flows, measuring the required parameters of said flows to determine their fibre mass flow rates and determining the fibre mass flow rates, fractionating each of said flows by a screen into a retained and a through screen fraction, the screening means for one of said two flows having a different mesh size than the screening means for the other of said two flows, each of said mesh sizes having a retained average fibre length equivalent to a pre-determined laboratory fibre classifier retained fraction average fibre length, measuring the required parameters of a selected one of said retained or through screen fractions for each of said screening means to determine their fibre mass flow rates and determining the fibre mass flow rates of said selected retained or through screened fractions, determining the laboratory fibre classifier fibre length distribution of said pulp based on: (1) said determined fibre mass flow rates, (2) said equivalent laboratory fibre classifier retained fraction average fibre length for each of said mesh sizes, and (3) a cumulative normal probability relationship for said pulp between said laboratory fibre classifier retained fraction average fibre lengths, and cumulative retained fractions by weight as a % of feed to said screening means.

2. A method as defined in claim 1 wherein said fiber mass flow rates of said two flows are substantially equal.

3. A method as defined in claim 2 wherein said fibre mass flow rates of said selected fractions are determined based on the consistency and rate of flow of said selected fractions.

4. An apparatus for on line determining the fibre length distribution by weight of a pulp comprising, means for feeding said pulp as two flowing screens, means for measuring the parameters of said streams required to determine the fibre mass flow rates of said streams, screening means of a first mesh size for fractionating one of said two streams into a retained and a through fraction, screening means of a second mesh size significantly different from said first mesh size for fractionating the other of said two streams into a second retained and through fraction, said mesh sizes each having a retained average fibre length equivalent to a pre-determined laboratory fibre classifier retained fraction average fibre length, means for measuring the required parameters of a selected one of said retained fractions and said through fractions for each of said screening means for determining their fibre mass flow rates, means for determining the fibre mass flow rates of said selected fractions, means for determining the laboratory fibre classifier fibre length distribution by weight of said pulp based on: (1) said equivalent average laboratory fibre classifier fibre length for each of said mesh sizes, (2) the fibre mass flow of said selected fractions (3), the fibre mass flow rates of said two streams, and (4) a cumulative normal probability distribution relationship for said pulp between said laboratory fibre classifier fibre lengths and cumulative retained fractions by weight as a % of feed to said screening means.

5. An apparatus as defined in claim 4 wherein said mesh sizes are between 30 and 50.

6. An apparatus as defined in claim 5 wherein said mesh sizes are between 35 and 45.

7. An apparatus as defined in claim 4 wherein said first mesh size is 41 mesh and said second mesh size is 35.

* * * * *